United States Patent [19]

Foster et al.

[11] Patent Number: 5,736,151

[45] Date of Patent: Apr. 7, 1998

[54] ANTIBIOTIC OIL SUSPENSIONS

[75] Inventors: Todd P. Foster, Kalamazoo; David L. Kiefer, Alanson, both of Mich.

[73] Assignee: Pharmacia & Upjohn Company, Kalamazoo, Mich.

[21] Appl. No.: 806,584

[22] Filed: Dec. 9, 1996

[51] Int. Cl.$^6$ ............................ A61F 2/02; A61K 31/545
[52] U.S. Cl. ................................. 424/423; 514/206
[58] Field of Search ........................ 424/423; 514/206; 540/227

[56] References Cited

U.S. PATENT DOCUMENTS

| | | |
|---|---|---|
| 4,464,367 | 8/1984 | Labeeuw . |
| 4,877,782 | 10/1989 | Cazers et al. ............... 514/206 |
| 4,902,683 | 2/1990 | Amin . |
| 4,937,330 | 6/1990 | Sacks . |
| 5,134,137 | 7/1992 | Cazers et al. ............... 514/206 |
| 5,223,496 | 6/1993 | Cazers et al. ............... 514/206 |

OTHER PUBLICATIONS

Amin, M.L., et al., J. Pharm. Sci., vol. 76(11):S255 (1976).
Evans, R.A., et al., "Certiofur Hydrochloride, A New Broad-Spectrum Cephalosporin: Effectiveness Against Induced Haemophilus Pleuropneumoniae of Growing Swine," Proceedings of the International Pig Veterinary Society, 10th Congress, Rio de Janeiro, Brazil, p. 94 (1988).

Evans, R.A., et al., "Effectiveness of Ceftiofur Hydrochloride, A New Broad-Spectrum Cephalosporin, in Treatment of Colibacillosis in Neonatal Swine," Proceedings of the International Pig Veterinary Society, 10th Congress, Rio de Janeiro, Brazil, p. 108 (1988).

*Primary Examiner*—Carlos Azpuru
*Attorney, Agent, or Firm*—Martha A. Gammill

[57] ABSTRACT

The present invention provides for the inclusion of small amounts of water in oil suspensions of active drugs, such as ceftiofur hydrochloride of formula I. The resulting suspensions have improved resuspendability. Improved resuspendability results in an improved product because less shaking of the suspension is required before dosing.

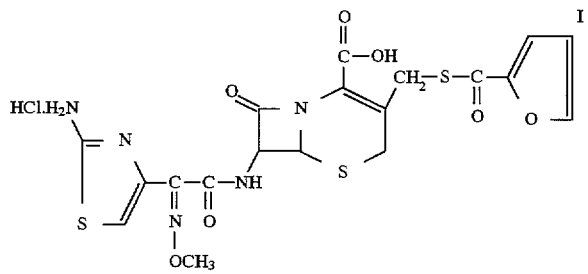

23 Claims, 1 Drawing Sheet

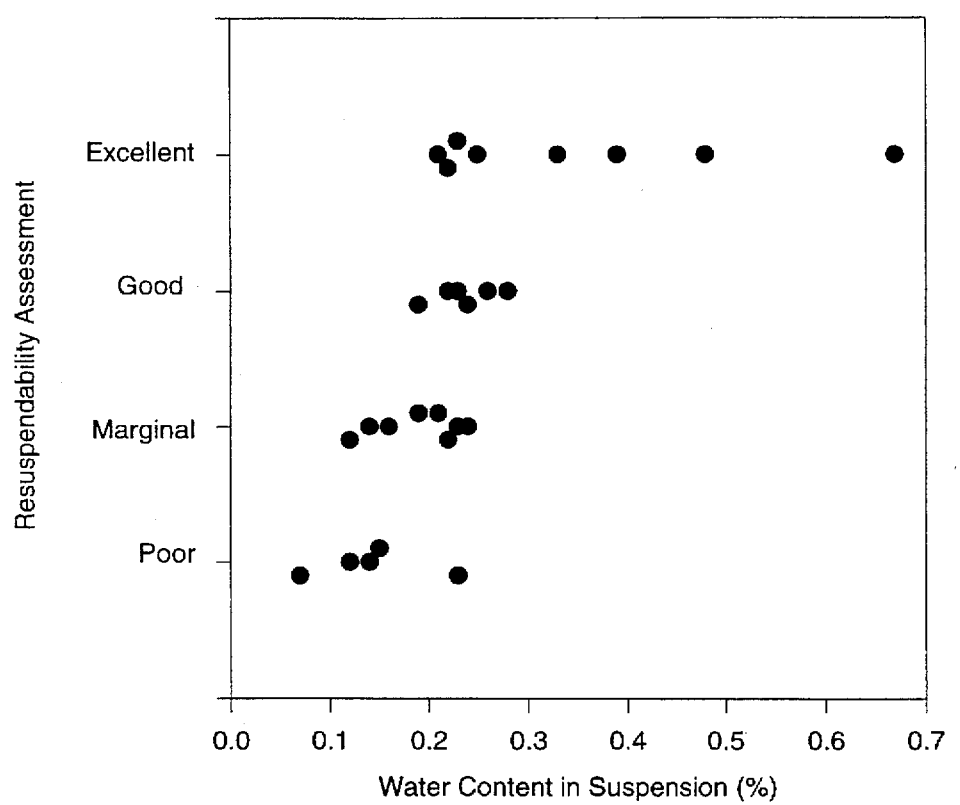
Figure 1. Resuspendability of Lots at Different Water Contents

ANTIBIOTIC OIL SUSPENSIONS

FIELD OF THE INVENTION

The present invention provides for novel pharmaceutical compositions of active drugs. More particularly, the present invention provides for novel formulations, such as oil suspensions, of the class of drugs known as cephalosporins. Most particularly, the present invention provides for novel oil suspensions of the cephalosporin, ceftiofur hydrochloride, which have improved properties, such as physical stability (i.e., resuspendability).

BACKGROUND OF THE INVENTION

The following five references: W. I. Higuchi, J. Swarbrick, H. F. H. Ho, A. P. Simonelli and A. Martin, Particle phenomena and coarse dispersions, in *Remington's Pharmaceutical Sciences*, 17th Edition, 1985, Mack Publishing Company, Easton, Pa., pp. 301–329; M. J. Falkiewicz, Theory of Suspensions, in *Pharmaceutical Dosage Forms: Disperse Systems*, Volume 1, Eds. H. A. Lieberman, M. M. Rieger and G. S. Banker, 1988, Marcel Dekker, New York, N.Y., pp. 13–48; R. A. Nash, Pharmaceutical Suspensions, in *Pharmaceutical Dosage Forms: Disperse Systems*, Volume 1, Eds. H. A. Lieberman, M. M. Rieger and G. S. Banker, 1988, Marcel Dekker, New York, N.Y., pp. 151–198; N. K. Patel, L. Kennon and R. S. Levinson, Pharmaceutical Suspensions, in *The Theory and Practice of Industrial Pharmacy*, Eds. L. Lachman, H. A. Lieberman and J. L. Kanig, 1986, Lea and Febiger, Philadelphia, Pa., pp. 479–501; and S. E. Tabibi and C. T. Rhodes, Disperse Systems, in *Modern Pharmaceutics*, Third Edition, Revised and Expanded, Eds. G. S. Banker and C. T. Rhodes, 1996, Marcel Dekker, New York, N.Y., pp. 310–319; are general textbook discussions on suspensions and the formulation of physically stable suspensions. Remington's states at page 313 the major challenge with developing a good suspension is obtaining physical stability: "The three major problem areas associated with suspensions are (1) adequate dispersion of the particles in the vehicle, (2) settling of the dispersed particles, and (3) caking of these particles in the sediment so as to resist redispersion."

It is generally recognized in the art that controlled particle-to-particle interaction is a method to produce physically stable suspensions. Coarse Dispersions: Suspensions, Emulsions and Semisolids, in *Physical Pharmacy*, 2nd Edition, Eds. A. N. Martin, J. Swarbrick and A. Cammarata, 1969, Henry Kimpton Publishers, London, England, pp. 522–525; see also E. N. Hiestand, Theory of Coarse Suspension Formulation, *Journal of Pharmaceutical Sciences*, 1964, 53(1): 1–18, especially pages 9–12. Many investigators refer to this controlled aggregation as "flocculation." The particle interaction must result in a "loose" particle aggregation so when the suspension is shaken the particles can separate to some extent and a uniform dose can be obtained. The particle attraction must be "strong" enough so particle aggregation does occur. However, the particle aggregation cannot be so "strong" that the particles will never separate. Proper particle flocculation allows particles to settle with high sedimentation volumes and not to pack or cake drug at the bottom of the container. *Physical Pharmacy* (cited above) at pages 522–525; E. N. Hiestand (cited above) at pages 9–12; and W. I. Higuchi et al. (cited above) at page 315, FIGS. 21–19.

These five general chapters/articles mention several additives which cause suspensions to flocculate. These flocculating agents include electrolytes, surfactants and polymers. E. N. Hiestand (cited above) at pages 13–15; and *Physical Pharmacy* (cited above) at pages 522–525. Surfactant examples include polyoxyethylene ethers of mixed partial fatty acid esters of sorbitol anhydrides (Tweens), the same compounds without the hydrophilic oxyethylene groups (Spans), higher molecular weight polyethylene glycols (Carbowaxes) and molecular combinations of polyoxyethylene and polyoxypropylene (Pluronics). N. K. Patel et al. (cited above) at page 489. Electrolyte examples include sodium chloride, potassium chloride and calcium salts as well as sulfates, citrates and phosphates. R. A. Nash (cited above) at page 183. Polymers may include gelatin, natural gums like tragacanth and xanthan, and cellulose derivatives like sodium carboxymethylcellulose, hydroxypropylcellulose and hydroxypropylmethylcellulose. R. A. Nash (cited above) at page 184. None of the five review articles discuss the importance of water alone in causing particle-to-particle interaction (or in decreasing particle-to-particle repulsion) when formulating a pharmaceutical suspension.

E. N. Hiestand (cited above) at page 14, discloses that, in the paint industry particularly, oil suspension formulations were prepared using liquids, such as water, as flocculating agents. Also at page 14, Hiestand describes the usefulness of water in pharmaceutical suspensions; however, he does not give any specifics on the drug or the vehicle to be used. Certainly, he does not mention the use of an oil vehicle. He also states that a surface-active material (e.g., surfactant) should be included in the suspension to coat the lyophobic drug surface.

The following four references discuss how small amounts of water in hydrophobic vehicles (e.g., organic solvents, oils), especially those used in the paint and printing ink industry, cause flocculation: C. R. Bloomquist and R. S. Shutt, Fine Particle Suspensions in Organic Liquids, *Industrial and Engineering Chemistry*, June, 1940, 32(6): 827–831; F. H. Rhodes and W. J. Jebens, Studies in the Plasticity of Paints, *Journal of Physical Chemistry*, 1930, 35: 383–404; H. R. Kruyt and F. G. Van Selms, The Influence of a Third Phase on the Rheology of Suspensions, *Rec. Trav. Chim.*, 1943, 62: 415–426; and A. C. Zettlemoyer, Modern Techniques for Investigating Interactions with Surfaces, *Chem. Rev.*, 1959, 59: 937–981.

The following more specific prior art references discuss the dispersion of a drug in oil to produce a suspension: J. Heidt, Injectable Suspensions Containing Maleic Acid or a Salt Thereof as a Stabilizing Agent, UK Patent Application 2 105 589 A, published 30 Mar. 1983; A. L. Adjei, S. Borodkin and R. B. Doyle, Anhydrous Oil-Based Liquid Suspension for Delivering a Medicament, International Publication Number WO 91/08734, published 27 Jun. 1991; K. Bauer, K. E. Fetting, R. Gonnert, H. Thomas and H. Voege, New Niclosamide Suspension Formulations, UK Patent 1 527 638, published 4 Oct. 1978; and K. S. E. Su, J. F. Quay, K. M. Capanale and J. F. Stucky, Nonaqueous Cephalosporin Suspension for Parenteral Administration: Cefazolin Sodium, *Journal of Pharmaceutical Sciences*, 1984, 73(11): 1602–1606. None of these references mention the addition of water to oil formulations or discuss the importance small amounts of water have on resuspendability.

For example, Heidt claimed a suspension of an active ingredient in a neutral oil that contains maleic acid or a salt thereof to aid in resuspendability. The Adjei et al. patent provides general information on oil suspensions for the administration of drugs which are sensitive to water or which have an unpalatable taste and explains why certain ingredients are added to obtain a good suspension product. In referring to their oil suspension formulation, Adjei et al.

states at page 3: "In a preferred embodiment, the formulation also contains a drying agent to help bind any residual water that would otherwise degrade the active therapeutic agent." Bauer et al. obtained a specific patent for niclosamide (which is an anthelmintic agent) and its salts in an oil-based suspension. The forms of niclosamide which may be used include its anhydrous form, its form which contains water of crystallization, as well as its other salt forms. Su et al. studied the suspension characteristics of the cephalosporin compound, cefazolin sodium, dispersed in peanut oil and ethyl oleate (i.e., lipophilic or oleaginous carriers). This article stated that while water is generally the preferred suspending liquid, some physiologically active agents such as the cephalosporin antibiotics are not chemically stable in water-based parenteral pharmaceutical suspensions. Therefore, according to the article, to achieve a ready-to-use cephalosporin preparation which can be stored at room temperature, it is desirable to develop a satisfactory suspension utilizing a nonaqueous liquid as the suspending medium.

The following two pharmaceutical articles: D. J. A. Crommelin and C. J. de Blaey, In Vitro Release Studies on Drugs Suspended in Non-Polar Media I. Release of Sodium Chloride from Suspensions in Liquid Paraffin, *International Journal of Pharmaceutics,* 1980, 5:305–316; and D. J. A. Crommelin and C. J. de Blaey, In Vitro Release Studies on Drugs Suspended in Non-Polar Media II. The Release of Paracetamol and Chloramphenicol from Suspensions in Liquid Paraffin, *International Journal of Pharmaceutics,* 1980, 6:29–42; discussed the addition of small amounts of water (0.01 or 0.05% m/m) to liquid paraffin suspensions (ie. mineral oil) which contain sodium chloride, paracetamol or chloramphenicol. Water was added to the oil suspensions to observe the influence of the water on in vitro drug release. The addition of water to the sodium chloride suspension significantly enhanced the release rate. The addition of water to the other two suspensions did not change the release rate. The enhanced agglomeration of the particles when water was added to any of the three suspensions was also described.

The Crommelin and de Blaey papers refer to colloidal dispersion research conducted in the 1960's where the influence of water on dispersions in nonpolar media was studied. The following two papers: D. N. L. McGown, G. D. Parfitt and E. Willis, Stability of Non-aqueous Dispersions I. The Relationship between Surface Potential and Stability in Hydrocarbon Media, *Journal of Colloid Science,* 1965, 20:650–664; and A. Kitahara, S. Karasawa and H. Yamada, The Effect of Water on Electrokinetic Potential and Stability of Suspensions in Nonpolar Media, *Journal of Colloid and Interface Science,* 1967, 25:490–495; examined dispersants like alpha-alumina, carbon black, copper phthalocynanine green pigment or barium sulfate in nonpolar solvents such as p-xylene, n-heptane, cyclohexane or benzene which contain different amounts of surfactants (e.g. Aerosol TO (sodium di-2-ethylhexyl sulfosuccinate), polyoxyethylene nonylphenol ether). The amounts of water added were small, normally less than 400 ppm. These researchers noticed changes in physical stability, zeta potential and turbidity with different amounts of added water. However, they also stated that adding water may not result in changes for all systems as they noted no effect when adding water to carbon black or barium sulfate in cyclohexane or n-heptane solutions of polyoxyethylene nonylphenol ether. They also observed the formation of unstable colloidal dispersions when water was added to these systems in excess of 400 ppm.

Thus, as documented above, the problem in the art has been to develop pharmaceutically useful suspensions of drugs, which are also physically stable (i.e., resuspendable). Attempts to solve this problem have not focused on the addition of water to such suspensions, and in fact, for cephalosporins, have taught away from its use.

INFORMATION DISCLOSURE

EXCENEL® Sterile Suspension (ceftiofur hydrochloride) is currently marketed in the U.S. as a ready-to-use oil suspension product for the treatment/control of swine bacterial respiratory disease. The ingredients of this currently marketed formulation are listed below. No water is added to this formulation, but its ingredients may contain a small amount of water, as will be described further below. This formulation of ceftiofur hydrochloride has several disadvantages, such as poor physical stability (i.e., resuspendability).

Published articles, such as the following, demonstrate the effectiveness of EXCENEL® Sterile Suspension as a veterinary antibiotic: "Ceftiofur Hydrochloride, a New Broad-Spectrum Cephalosporin: Effectiveness Against Induced-Haemophilus pleuropneumonia of Growing Swine," and "Effectiveness of Ceftiofur Hydrochloride, a New Broad-Spectrum Cephalosporin, in Treatment of Colibacillosis in Neonatal Swine," Proceedings of the International Pig Veterinary Society, 10th Congress, Rio de Janeiro, Brazil; pp. 94 and 108, respectively (1988). M. I. Amin et al., "Radiation Sterilization of Suspension Ceftiofur Hydrochloride," J. Pharm. Sci., Vol. 76(11) :S255 (1976), evaluated methods for sterilizing ceftiofur hydrochloride powder and a suspension formulation containing 3% lecithin coated ceftiofur hydrochloride.

NAXCEL/EXCENEL® Sterile Powder (ceftiofur sodium) is also currently marketed throughout the world for the treatment/control of bovine and swine bacterial respiratory diseases. This product must be reconstituted with sterile water before it is injected into the animal.

Amin et al., Crystalline Cephalosporin Hydrohalide Salts, U.S. Pat. No. 4,902,683, 20 Feb. 1990, discloses crystalline hydrochloride and hydrobromide salts of the cephalosporin antibiotic, ceftiofur, processes for their manufacture, and pharmaceutical compositions thereof. None of the compositions disclosed therein teach or suggest the addition of water.

Labeeuw et al., Cephalosporin Derivatives, Process for Preparation Thereof and Drugs Containing Said Derivatives Usable as Antibiotics, U.S. Pat. No. 4,464,367, 7 Aug. 1984, discloses the cephalosporin antibiotic, ceftiofur, as well as alkali, alkaline earth and amine salts thereof. This patent discloses as an apparently prophetic example of a pharmaceutical composition, ampoules containing the sodium salt of ceftiofur and water (which would be a solution) for an injectable preparation. However, there is no indication that such a composition would actually work, and in fact, it is believed that any such water solution would not be marketable because of chemical instability.

Dill et al., Conversion of Cephalosporin Hydrohalide Salt to Alkali Metal Salt, U.S. Pat. No. 4,937,330, 26 Jun. 1990, discloses a process for making a alkali metal salt of ceftiofur, such as the sodium salt, by the following steps: a) neutralizing a hydrohalide salt of ceftiofur, such as the hydrochloride salt, in an aqueous organic solvent, by treating it with a basic resin; b) filtering the obtained solution to remove the basic resin; and c) treating the filtrate with a base of an alkali metal.

No where do these references teach or suggest the addition of water to oil suspensions of cephalosporins, such as ceftiofur hydrochloride. Furthermore, the addition of water, according to the present invention, resulted in unexpected improvements in the physcial properties of the suspension, such as physical stability (i.e., resuspendability) and shelf-life, as will be described further below.

SUMMARY OF THE INVENTION

The present invention particularly provides:

In an oil suspension of ceftiofur hydrochloride in unit dosage form consisting of an effective amount of ceftiofur hydrochloride, a biocompatible oil and one or more pharmaceutically acceptable excipients, the improvement characterized by: an amount of water which is present at about 0.25% to about 20.20% of the suspension; preferably, the water is present at about 0.25% to about 2.20% of the suspension; more preferably, the water is present at about 0.30% to about 0.75% of the suspension; most preferably, the water is present at about 0.30% to about 0.50% of the suspension.

The present invention also provides:

In a pharmaceutical composition containing ceftiofur hydrochloride, the improvement characterized by: the addition of water. The water is added in an amount which is about 0.5 to about 200 mg of water per ml of composition. Preferably, the water is added in an amount which is about 0.5 to about 20 mg of water per ml of composition. More preferably, the water is added in an amount which is about 1 to about 5.5 mg of water per ml of composition. Most preferably, the water is added in an amount which is about 1 to about 3 mg of water per ml of composition.

Finally, the present invention provides:

A pharmaceutical composition in unit dosage form, which comprises:

a) a drug, b) a biocompatible oil, and c) water which is present at about 0.25% to about 20.20% of the composition. Preferably, the water is present at about 0.25% to about 2.20% of the composition. More preferably, the water is present at about 0.30% to about 0.75% of the composition. Most preferably, the water is present at about 0.30% to about 0.50% of the composition.

The drug in this composition may be an antibiotic such as spectinomycin. The drug in this composition may also be a cephalosporin such as ceftiofur hydrochloride. The ceftiofur hydrochloride may have a particle size of less than 10 microns and may be present at a concentration of about 50 mg per ml of composition.

The biocompatible oil in this composition may be selected from the group consisting of: canola oil, corn oil, cottonseed oil, olive oil, peanut oil, sesame oil, soybean oil, safflower oil, coconut oil, sunflower oil and palm oil. Cottonseed oil is preferred.

This composition may also contain one or more pharmaceutically acceptable excipients, such as Phospholipon and sorbitan monooleate.

This composition may be an injectable oil suspension.

In general, the present invention provides an oil suspension of an active drug which also contains added water.

Drugs which may be formulated in the suspension of the present invention include the following cephalosporins: First generation (ceftiofur, cefadroxil, cephalexin, cefazolin); Second generation (cefaclor, cefuroxime, cefotetan, cefamandole, cefoxitin, cefonicid, cefmetazole); and Third generation (ceftizoxime, cefoperazone, cefprozil, ceftazidime, cefotaxime, ceftriaxone, cefixime, cefpodoxime).

Other drugs which may also be formulated in the suspension of the present invention include the following: Aids Related Complex Therapeutic Agents (trimethoprim, sulfamethoxazole, zidovudine, dianosine, delavirdine); Analgesics (aetaminophen, aspirin, ibuprofen, naproxen); Antacids (aluminum hydroxide, magnesium hydroxide, simethicone); Antibiotics (spectinomycin, gentamicin, erythromycin, penicillins, quinolones, sulfonamides, tetracyclines); Antihistamines (hydroxyzine, diphenhydramine, loratadine); Cardiovascular agents (prazosin, methyldopa, captopril, propranolol, isosorbide dinitrate, verapamil, furosemide); Cough and Cold preparations (pseudoephedrine, dextromethorphan, chlorpheniramine); Dermatologicals (clindamycin, tretinoin, hydrocortisone, ketoconazole, miconazole); Diabetes agents (glyburide, chlorpropamide); Diarrhea medications (loperamide); Hormones (estrogens, growth hormone, methylprednisolone); Hypolipidemics (colestipol, lovastatin); Nausea medications (meclizine, prochlorperazine); Otic preparations (neomycin, polymyxin B sulfates); Parkinsonism drugs (bromocriptine, benztropine); Psycotropics (chlordiazepoxide, diazepam, triazolam, imipramine).

As described above, the present invention provides for a formulation which is an oil suspension containing a cephalosporin with added water. More specifically, the present invention provides for the inclusion of small amounts of water in oil suspensions of the cephalosporin, ceftiofur, particularly ceftiofur hydrochloride. The resulting suspensions have improved resuspendability. Improved resuspendability results in an improved product because less shaking of the suspension is required before dosing and allows the product to be stored longer (i.e., longer shelf-life) because the drug in the product will not settle and compact. The addition of water may also eliminate the need for including other formulation agents, such as viscosity-enhancing suspending agents (e.g., gelling agents).

The structure of ceftiofur hydrochloride is Formula I as follows:

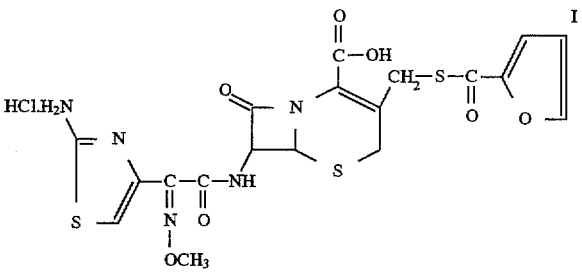

This compound is a crystalline hydrochloride salt of 7-[2-(2-amino-1,3-thiazol-4-yl)-2-methoxyimino) acetamido]-3-[(fur-2-ylcarbonyl)thiomethyl]-3-cephem-4-carboxylic acid. This cephalosporin free acid compound is known by the generic name, ceftiofur. Its preparation is described in U.S. Pat. No. 4,902,683, Amin et al., 20 Feb. 1990, which is hereby incorporated by reference.

The amount of water which is to be added to obtain the suspension of the present invention ranges from about 0.5 to about 200 mg of water per ml of formulation; preferably about 0.5 to about 20 mg of water per ml of formulation is added; more preferably about 1 to about 5.5 mg of water per ml of formulation is added; most preferably, about 1 to about 3 mg of water per ml of formulation is added.

As described above, the formulation of the present invention consists of an active drug ingredient, such as the cephalosporin ceftiofur hydrochloride, a biocompatible oil and water. The biocompatible oil is composed essentially of triglycerides, which are long chain fatty acid esters of glycerol, or mixtures of triglycerides and fatty acids. Trihydroxy, dihydroxy, monohydroxy or even polyhydroxy compounds may be substituted for the glycerol. The oils may be of vegetable, animal or synthetic origin. Preferred oils include canola, corn, cottonseed, olive, peanut, sesame, soybean, safflower, coconut, sunflower, and palm. The especially preferred oil is cottonseed oil.

The concentration of the cephalosporin in the formulation of the present invention may vary between about 1 mg/ml to 500 mg/ml. Preferably, for ceftiofur hydrochloride, the concentration is about 50 mg/ml. In general, the upper limit on the concentration is determined by when the oil composition becomes too viscous to syringe.

The suspension of the present invention may also contain other pharmaceutically acceptable excipients normally included in such suspensions, for example, suspending agents, preservatives, wetting agents or flocculating agents, if desired. Suspending agents, such as gums (e.g., acacia, carrageenan, sodium alginate and tragacanth), cellulosics (e.g., sodium carboxymethylcellulose, microcrystalline cellulose, and hydroxyethylcellulose), and clays (e.g., bentonite and colloidal magnesium aluminum) may be included. Preservatives, such as methyl and propyl paraben, benzyl alcohol, chlorobutanol and thimerosal may be added. Wetting agents such as anionic (e.g., docusate sodium and sodium lauryl sulfate) and nonionic (polysorbates, polyoxamers, octoxynol-9) surfactants may be used. Thickeners, such as gelatin, natural gums and cellulose derivatives (such as those listed above as suspending agents) may be added. Buffers, such as citrate and phosphate buffering agents, may be included, as well as osmotic agents, such as sodium chloride and mannitol. For oral suspensions, additional agents may be used, such as the following: flavoring agents, sweeteners (e.g., mannitol, sucrose, sorbitol and dextrose), colorants and fragrances. Particularly, for the formulations of the present invention, excipients such as sorbitan monooleate (which may be used as a wetting agent) and Phospholipon (which may be used as a dispersant) may be added.

The suspension of the present invention may be prepared by any method known in the art for the preparation of injectable suspensions. All such methods involve the active ingredient being present in a suitable solid form and suspension thereof in a liquid vehicle. However, if the formulation contains Phospholipon, the Phospholipon may be added via a heating and cooling step, which may be considered different from a typical suspension manufacture.

The preparation of a 5 L batch of the ceftiofur hydrochloride suspension of the present invention is shown in EXAMPLE 1 below. Micronized ceftiofur HCl, which consists of particles with a median geometric mean below 10 microns, may be preferably used. However, as one skilled in the art realizes, the particle size may vary above and below the preferred size depending on the cephalosporin, the biocompatible oil and any other ingredients used in the composition. In fact, nonmicronized drug may be used in some embodiments.

A manufacturing facility suitable for producing sterile products must be used if one is making this composition as an injectable for commercial use. Also, all manufacturing equipment and packaging components should be sterilized when making the suspension for administration by injection.

The suspension of the present invention, which contains ceftiofur hydrochloride as its active ingredient, is useful as an antibiotic to cure bacterial infections of animals, such as livestock and poultry. Ceftiofur hydrochloride is a broad spectrum cephalosporin antibiotic active against gram-positive and gram-negative bacteria, including beta-lactamase-producing strains. For animals, it is effective in swine against a variety of diseases, such as diarrhea, pneumonia (*Actinobacillus pleuropneumoniae, Pasteurella multocida, Salmonella choleraesuis* and *Streptococcus suis* type 2), transmissible gastro enteritos; avian pneumonia (*mycoplasma, haemophilus*) and Marek's diseases; and is effective in cattle against a variety of diseases, such as bovine diarrhea, pneumonia and mastitis.

The effective amount of this antibiotic to be used will vary depending on the species, age and/or weight of the animal being treated. It could vary between about 0.1 and 100 mg/kg. For example, when treating swine bacterial respiratory disease (swine bacterial pneumonia, SBP), the dose may range between about 3 and 5 mg/kg given once daily for three consecutive days.

Also, the concentration of the oil composition will depend on the species to be treated and the dose of antibiotic required. For example, when treating SBP at a dose of 3 mg/kg, a 50 mg/mL concentration solution is preferred. One injection of 1.0 mL will provide the required composition for each 22–37 pound body weight.

The routes of administration include oral and parenteral, such as subcutaneous and intramuscular. The preferred route of administration in livestock is subcutaneous. However, other parenteral routes of administration, like intramuscular, may be used.

Furthermore, those skilled in the art would know how to formulate the composition of the present invention, using pharmaceutically acceptable excipients, into appropriate unit dosage forms. The term "unit dosage form" refers to physically discrete units suitable as unitary dosages for mammalian subjects, each unit containing as the essential active ingredient a predetermined quantity of the drug of this invention with the required pharmaceutical means which adapt said ingredient for systemic administration. Examples of such dosage forms include oral formulations, such as tablets or capsules, or parenteral formulations, such as injectable suspensions.

Additional information on the dosage and mode of administration of the antibiotic ceftiofur hydrochloride is contained in U.S. Pat. No. 4,902,683, which is hereby incorporated by reference herein.

In the present invention, the addition of water to the ceftiofur hydrochloride suspension causes the particles to flocculate and settle in the suspension, resulting in an improved and pharmaceutically useful suspension. This enhanced flocculation (i.e., aggregation) observed when adding small amounts of water to ceftiofur oil suspensions results in a suspension that resuspends more easily. The improved properties of the suspension of the present invention is further detailed in EXAMPLE 2 below.

The currently marketed formulation of ceftiofur hydrochloride, known as EXCENEL® Sterile Suspension, contains the following ingredients per mL:

| | |
|---|---|
| Ceftiofur HCl micronized | 50 mg* |
| Phospholipon 90-H (lecithin) | 0.50 mg |
| Sorbitan monooleate NF | 1.50 mg |
| Cottonseed oil NF | enough to make 1 mL |

*This is the amount of ceftiofur activity.

No water is added to this formulation; however, water may be present in its other ingredients (e.g., bulk ceftiofur hydrochloride and cottonseed oil) and/or due to environmental conditions. As currently manufactured and sold, the total amount of water which has been measured as being present in this formulation ranges from about 0.1% to 0.2% (which is about 1 to 2 mg of water per ml of formulation).

A ceftiofur hydrochloride formulation of the present invention has the following ingredients:

| Ceftiofur HCl micronized | 50 mg* |
|---|---|
| Water for Injection, USP | 20 mg |
| Cottonseed oil NF | enough to make 1 mL |

*This is the amount of ceftiofur activity.

An important difference between the formulation of the present invention and the formulation that is currently marketed is that water is added to the formulation of the present invention—in addition to that which may already be present, as noted above. Assuming the currently marketed formulation contains about 2.0 mg of water per ml of formulation (which is the upper limit which has been identified, as noted above), the amount of water which is added to obtain the suspension of the present invention ranges from about 0.5 to about 200 mg of water per ml of formulation; preferably about 0.5 to about 20 mg of water per ml of formulation is added; more preferably about 1 to about 5.5 mg of water per ml of formulation is added; most preferably, about 1 to about 3 mg of water per ml of formulation is added.

Thus, the resulting formulation of the present invention will have a total amount of water of about 0.25% to about 20.20% (which is about 2.5 to about 202.0 mg of water per ml of formulation). Preferably, the resulting formulation of the present invention will have a total amount of water of about 0.25% to about 2.20% (which is about 2.5 to about 22.0 mg of water per ml of formulation). More preferably, it will have a total amount of water of about 0.30% to about 0.75% (which is about 3.0 to about 7.5 mg of water per ml of formulation). Most preferably, it will have a total amount of water of about 0.30% to about 0.50% (which is about 3.0 to about 5.0 mg of water per ml of formulation).

Surprisingly and unexpectedly, the addition of this small amount of water results in a ceftiofur hydrochloride formulation with substantially improved properties, as documented below.

A preferred ceftiofur hydrochloride formulation of the present invention has the following ingredients:

| Ceftiofur HCl micronized | 50 mg* |
|---|---|
| Phospholipon 90-H (lecithin) | 0.50 mg |
| Sorbitan monooleate NF | 1.50 mg |
| Water for Injection, USP | 2.50 mg |
| Cottonseed oil NF | enough to make 1 mL |

*This is the amount of ceftiofur activity.

The unexpected differences in the properties of these two formulations are documented in EXAMPLE 2 below.

DESCRIPTION OF THE PREFERRED EMBODIMENTS

EXAMPLE 1

Ceftiofur Hydrochloride Oil Suspension—Water Added (5 L Batch)

The ingredients listed in Table 1 are secured:

TABLE 1

| Amounts Required for a 5 L Batch | | |
|---|---|---|
| Ingredient | Amount | Amount per mL |
| Ceftiofur HCl micronized | 0.258 kg* | 50 mg |
| Phospholipon-90H | 0.25 g | 0.5 mg |
| Sorbitan monooleate NF | 0.75 g | 1.5 mg |
| Water for Injection, USP | 1.25 g | 2.5 mg |
| Cottonseed Oil | q.s. to 5 L | q.s. to 1 mL |

*The amount is of active ceftiofur taking into consideration the salt.

Assumes 100% potent ceftiofur HCl with 3.2% w/w of the weight accounting for the HCl. MW of ceftiofur HCl is 560.0.

The required weight or volume of oil is placed into a glass or stainless steel vessel. (See Table 1 for the amounts required for a 5 L batch.) For a 5 L batch, 4.5 L of cottonseed oil is used to begin. The oil is heated to above 100° C. and the required amount of Phospholipon (lecithin) is added and stirred until dissolved. The time required for the Phospholipon (lecithin) to dissolve depends on the temperature, mixing, and size of the batch. It normally dissolves within 1 to 60 minutes. The oil containing the Phospholipon is then cooled. Once cooled the sorbitan monooleate is added and mixed. Next the ceftiofur HCl is added followed by mixing of 1 to 120 minutes. The length of mixing depends on the batch size, size of mixer and speed of mixing. Water is added and the suspension is mixed for 1 to 60 minutes.

The suspension is stored in the original manufacturing vessel as long as mixing continues to keep the drug suspended. It is then filled into vials using standard vial filling equipment. The vials are then closed with a stopper, capped, labeled and boxed.

EXAMPLE 2

Comparison of the Currently Marketed Formulation of Ceftiofur Hydrochloride and Formulations of the Present Invention A. Resuspendability or Physical Stability One of the most important differences observed between the fomulations was the greater physical stability or resuspendability when water was added to the formulation. Shown in FIG. 1 is a plot of resuspendability compared to the water content of various ceftiofur HCl suspensions.

It is clear from this figure that as the water content increased, the suspension resuspended better. The resuspendability of suspensions with lower water content was poor or, at best, variable. It was not until the water content was increased that consistently more resuspendable suspensions were achieved. More specific physical stability comparisons are shown in the next section.

Several other differences were observed when increasing the water content of the suspension. All these differences help explain why greater physical stability was observed when adding water: First, sedimentation volumes were greater, and the sedimentation rates faster when water was added. The sedimentation volume is the height of the sediment when compared to the height when the suspension is fully resuspended. Larger sedimentation volumes typically are associated with a suspension that resuspends better. Less packaging of the sediment occurs making it easier to resuspend (i.e., less energy needs to be put into the system via shaking).

Second, the faster settling rate indicates the particles are interacting to create a flocculated system. A flocculated suspension typically resuspends better then a nonflocculated suspension. The flocs that form will be larger then the original particles so they settle faster. But, because they interact with themselves and other flocs, they will not settle to such low sedimentation volumes. Thus, they are easier to resuspend. The addition of water to the formulation of the present invention caused flocculation and faster sedimentation rates were observed.

Also, flocculation was observed with particle size data. Larger measured particles were observed as the water content of the suspension increased. Furthermore, photomicrographs were taken showing the particles interacting to create larger flocs.

Finally, rheology differences were noted when adding water to the formulation. The rheology, or flow characteristics, changed from Newtonian to non-Newtonian with added water. The plastic systems found with added water indicate a structure was formed in the water-added suspensions. This added structure again indicates a flocculated system which will have improved resuspendability.

In summary, all of the differences found between the suspensions with and without added water indicate that physical stability will be better with the water-added formulation.

B. Chemical Stability and Shelf-life

The stability of suspensions, and ultimately their shelf-life, are based on both chemical and physical stability. The chemical stability is assessed to insure that the product does not become subpotent during use. The chemical stability of the current formulation (ie. non-water-added formulation) has been studied extensively. For example, shown in Table 2 is the stability through 3 years for 3 different batches of the current suspension.

TABLE 2

Chemical Stability of a 50 mg/mL Ceftiofur HCl Suspension with No Additional Water Added when Stored at 25° C.

| | Potency in mg/mL ± standard deviation | | |
|---|---|---|---|
| Time, months | Lot A | Lot B | Lot C |
| 0 | 49.8 ± 0.7 | 51.1 ± 0.5 | 50.5 ± 0.3 |
| 3 | 48.4 ± 1.3 | 49.4 ± 1.6 | 48.4 ± 0.4 |
| 6 | 48.1 ± 0.7 | 48.8 ± 1.2 | 48.6 ± 0.7 |
| 12 | 49.1 ± 0.4 | 50.2 ± 0.3 | 50.1 ± 0.3 |
| 18 | 46.5 ± 1.4 | 48.5 ± 0.7 | 48.5 ± 0.9 |
| 24 | 46.8 ± 4.2 | 48.8 ± 0.6 | 49.2 ± 2.7 |
| 36 | 49.1 ± 0.8 | 49.5 ± 0.4 | 48.6 ± 0.7 |

Usually pharmaceutical products are allowed to decrease 10% in potency during their shelf-life. Table 2 shows the current suspension is chemically stable even out to three years when stored at room temperatures.

The chemical stability has not been assessed for as long with the formulation of the present invention containing additional water. Shown in Table 3 is the comparison of two batches that were made identically except for the amount of water added. Similarly, Table 4 shows another comparison of two batches that only varied in water content.

TABLE 3

Comparison of Chemical Stability of Two Batches with Different Water Contents when Stored at 25° C.

| | Potency as a percent of label ± standard deviation | |
|---|---|---|
| Time, months | Lot D (0.20% total water) | Lot E (0.39% total water) |
| 0 | 103.2 ± 0.5 | 102.2 ± 0.2 |
| 2 | 103.2 ± 0.4 | 101.6 ± 0.0 |
| 4 | 103.6 ± 0.3 | 103.3 ± 1.3 |
| 6 | 103.7 ± 0.4 | 103.0 ± 0.2 |

TABLE 4

Comparison of Chemical Stability of Two Batches with Different Water Contents when Stored at 25° C.

| | Potency as a percent of label ± standard deviation | |
|---|---|---|
| Time, months | Lot F (0.14% total water) | Lot G (0.67% total water) |
| 0 | 104.5 ± 0.3 | 103.4 ± 0.6 |
| 2 | 104.6 ± 1.7 | 103.1 ± 0.1 |
| 4 | 105.5 ± 0.7 | 105.4 ± 0.5 |
| 6 | 103.5 ± 0.5 | 102.9 ± 0.1 |

Both Tables 3 and 4 show the suspension to be chemically stable. No difference was observed in chemical stability even with high water content. Thus, contrary to what may be expected, the addition of water did not adversely affect the chemical stability of the suspension. Additional stability data which was obtained at accelerated temperatures shows no difference in stability with higher water content.

C: Physical Stability

Physical stability is just as important as chemical stability. If the product does not resuspend adequately when shaken, the dose will be incorrect. With incomplete resuspension when shaken, the initial doses removed will be subpotent. This occurs because drug remains at the bottom of the vial preventing the correct concentration of the suspension when agitated. If part of the product is removed at a concentration significantly less then the labeled concentration, doses removed when the vial contains less product could become superpotent. This happens when further agitation removes drug from the bottom of the container and it is dispersed in the smaller volume of liquid.

The current formulation (ie. no water added) needs to be shaken, sometimes up to 60 seconds, before it becomes fully resuspended as shown in Table 5:

TABLE 5

Physical Stability of a 50 mg/mL Ceftiofur HCl Suspension with No Additional Water Added when Stored at 25° C.

| | Time Required to Fully Resuspend, Seconds | | |
|---|---|---|---|
| Time, months | Lot A | Lot B | Lot C |
| 0 | 10–20 | 10 | 10 |
| 3 | 30–40 | 10–20 | 20–30 |
| 6 | 30 | 10 | 20 |
| 12 | 50–60 | 20–30 | 40–50 |
| 18 | 40–60 | 20 | 30 |
| 24 | 50–60 | 60 | 40–60 |
| 36 | 60 | 40–50 | 60 |

It has been found that the addition of water improves the resuspendability characteristics of the suspension. A sensitive method for monitoring resuspendability is to use a 10-second mechanical shake assay. In this test, a vial is shaken for 10 seconds using a mechanical arm. A sample is removed from the suspension 2 cm below the liquid/air interface and assayed for the amount of drug. Shown in Tables 6 and 7 below are batches produced by identical methods except for the amount of water:

TABLE 6

Comparison of Physical Stability of Two Batches with Different Water Contents using a 10-Second Mechanical Shake Test Potency as a percent of label ± standard deviation

| Time, months | Lot D (0.20% total water) | Lot E (0.39% total water) |
|---|---|---|
| 0 | 82 ± 4 | 99 ± 2 |
| 2 | 72 ± 40 | 98 ± 1 |
| 4 | 48 ± 7 | 97 ± 2 |
| 6 | 49 ± 3 | 96 ± 1 |

TABLE 7

Comparison of Physical Stability of Two Batches with Different Water Contents using a 10-Second Mechanical Shake Test Potency as a percent of label ± standard deviation

| Time, months | Lot F (0.14% total water) | Lot G (0.67% total water) |
|---|---|---|
| 0 | 79 ± 5 | 104 ± 1 |
| 2 | 32 ± 21 | 101 ± 2 |
| 4 | 58 ± 16 | 102 ± 3 |
| 6 | 67 ± 27 | 95 ± 2 |

As the data from these tables shows, the increased water content improved resuspendability. The formulations with higher water concentrations were closer to the theoretical 100% of label and had less vial-to-vial variability (ie. tighter standard deviations).

BRIEF DESCRIPTION OF THE DRAWING

FIG. 1 is a plot of resuspendability compared to the water content of various ceftiofur HCl suspensions.

We claim:

1. In an oil suspension of ceftiofur hydrochloride in unit dosage form consisting of an effective amount of ceftiofur hydrochloride, a biocompatible oil and one or more pharmaceutically acceptable excipients, the improvement characterized by:

an amount of water which is present at about 0.25% to about 20.20% of the suspension.

2. The improvement of claim 1 wherein the water is present at about 0.25% to about 2.20% of the suspension.

3. The improvement of claim 2 wherein the water is present at about 0.30% to about 0.75% of the suspension.

4. The improvement of claim 3 wherein the water is present at about 0.30% to about 0.50% of the suspension.

5. In a pharmaceutical composition containing ceftiofur hydrochloride, the improvement characterized by:

the addition of water.

6. The improvement of claim 5 wherein the water is added in an amount which is about 0.5 to about 200 mg of water per ml of composition.

7. The improvement of claim 6 wherein the water is added in an amount which is about 0.5 to about 20 mg of water per ml of composition.

8. The improvement of claim 7 wherein the water is added in an amount which is about 1 to about 5.5 mg of water per ml of composition.

9. The improvement of claim 8 wherein the water is added in an amount which is about 1 to about 3 mg of water per ml of composition.

10. A pharmaceutical composition in unit dosage form, which comprises:

a) a drug, b) a biocompatible oil, and c) water which is present at about 0.25% to about 20.20% of the composition.

11. The composition of claim 10 wherein the water is present at about 0.25% to about 2.20% of the composition.

12. The composition of claim 11 wherein the water is present at about 0.30% to about 0.75% of the composition.

13. The composition of claim 12 wherein the water is present at about 0.30% to about 0.50% of the composition.

14. The composition of claim 10 wherein the drug is an antibiotic.

15. The composition of claim 14 wherein the antibiotic is spectinomycin.

16. The composition of claim 10 where the drug is a cephalosporin.

17. The composition of claim 16 wherein the drug is ceftiofur hydrochloride of formula I 18. The composition of claim 17 wherein the ceftiofur hydrochloride has a particle size of less than 10 microns and is present at a concentration of about 50 mg per ml of composition.

19. The composition of claim 10 wherein the oil is selected from the group consisting of: canola oil, corn oil, cottonseed oil, olive oil, peanut oil, sesame oil, soybean oil, safflower oil, coconut oil, sunflower oil and palm oil.

20. The composition of claim 19 wherein the oil is cottonseed oil.

21. The composition of claim 10 which further comprises one or more pharmaceutically acceptable excipients.

22. The composition of claim 21 wherein the excipients are lecithin and sorbitan monooleate.

23. The composition of claim 10 wherein the composition is an injectable oil suspension.

* * * * *